(12) United States Patent
Taurino et al.

(10) Patent No.: US 11,856,992 B2
(45) Date of Patent: Jan. 2, 2024

(54) AEROSOL-GENERATING SYSTEM, AEROSOL FORMING DEVICE AND A CARTRIDGE THEREFOR

(71) Applicant: PHILIP MORRIS PRODUCTS S.A., Neuchatel (CH)

(72) Inventors: Irene Taurino, Lausanne (CH); Ihar Nikolaevich Zinovik, Peseux (CH)

(73) Assignee: Philip Morris Products S.A., Neuchatel (CH)

( * ) Notice: Subject to any disclaimer, the term of this patent is extended or adjusted under 35 U.S.C. 154(b) by 518 days.

(21) Appl. No.: 17/055,199

(22) PCT Filed: Jun. 7, 2019

(86) PCT No.: PCT/EP2019/065034
§ 371 (c)(1),
(2) Date: Nov. 13, 2020

(87) PCT Pub. No.: WO2019/234245
PCT Pub. Date: Dec. 12, 2019

(65) Prior Publication Data
US 2021/0153552 A1    May 27, 2021

(30) Foreign Application Priority Data
Jun. 7, 2018  (EP) .................................. 18176642

(51) Int. Cl.
*A24F 40/465*    (2020.01)
*A61M 11/04*    (2006.01)
(Continued)

(52) U.S. Cl.
CPC ............ *A24F 40/465* (2020.01); *A24F 40/30* (2020.01); *A24F 40/42* (2020.01); *A61M 11/042* (2014.02); *A24F 40/10* (2020.01)

(58) Field of Classification Search
None
See application file for complete search history.

(56) References Cited

U.S. PATENT DOCUMENTS 10,863,770 B2    12/2020  Mironov
10,888,123 B2 *    1/2021  Silvestrini ............... A24F 40/42
(Continued)

FOREIGN PATENT DOCUMENTS

CN    104095291    1/2017
CN    107454700    12/2017
(Continued)

OTHER PUBLICATIONS

Search Report and Written Opinion for PCT/EP2019/065034 dated Jul. 25, 2019 (11 pages).
(Continued)

*Primary Examiner* — James Harvey
(74) *Attorney, Agent, or Firm* — Mueting Raasch Group (57) ABSTRACT

A cartridge (1) for an aerosol generating device, comprising a first cavity (13) containing a nicotine source and a second cavity (14) containing a lactic acid source, the first cavity and the second cavity defining an inner space between the cavities and an outer periphery of the cavities; and a susceptor comprising one or more susceptor elements, wherein the susceptor is arranged such that the susceptor is partly positioned in the inner space (16) between the cavities, and partly positioned in the outer periphery of the cavities, the outer periphery of the cavities being a space between the cavity walls and the cartridge walls.

15 Claims, 3 Drawing Sheets

(51) Int. Cl.
  *A24F 40/30* (2020.01)
  *A24F 40/42* (2020.01)
  *A24F 40/10* (2020.01)

(56) References Cited

U.S. PATENT DOCUMENTS 11,197,498 B2 * 12/2021 Waller .................... A24F 40/42
2018/0027883 A1    2/2018 Zuber
2021/0153552 A1 *  5/2021 Taurino ................ A24F 40/465

FOREIGN PATENT DOCUMENTS

| CN | 107809920 | 3/2018 | | |
| EP | 3183979 | * 12/2015 | ............. | A24F 47/00 |
| WO | WO 2013/098395 | 7/2013 | | |
| WO | WO 2015/101651 | 7/2015 | | |
| WO | WO 2017/108721 | 6/2017 | | |
| WO | WO 2017/108987 | 6/2017 | | |
| WO | WO 2017/129615 | 8/2017 | | |
| WO | WO 2017/129616 | 8/2017 | | |
| WO | WO 2019/030000 | 2/2019 | | |

OTHER PUBLICATIONS

Office Action issued in China for Application No. 201980032218.6 dated Aug. 18, 2023 (16 pages). English translation included.

* cited by examiner

AEROSOL-GENERATING SYSTEM, AEROSOL FORMING DEVICE AND A CARTRIDGE THEREFOR

This application is a U.S. National Stage Application of International Application No. PCT/EP2019/065034 filed Jun. 7, 2019, which was published in English on Dec. 12, 2019 as International Publication No. WO 2019/234245 A1. International Application No. PCT/EP2019/065034 claims priority to European Application No. 18176642.9 filed Jun. 7, 2018.

The present invention relates to aerosol generating systems comprising an aerosol generating device and a cartridge containing aerosol forming substrate in liquid form. In particular, the aerosol forming substrate comprises a nicotine source and a volatile delivery enhancing compound source for generating an aerosol comprising nicotine salt particles.

Known cartridges usually comprise two cavities. One cavity contains nicotine source, while the other contains volatile delivery enhancing compound, for example lactic acid. The nicotine source, the volatile delivery enhancing compound, or both may be carried by a carrier material.

Known aerosol generating devices usually comprise a power source, which provides power to an electrically operated heater. The heater may comprise a resistive heating element or a susceptor, for example. The heater is typically provided in the device or in the cartridge, and is positioned close to the cartridge or within the cartridge to heat the contents of the cavities and thus generate aerosol.

In the known devices, the heating of the cartridge may be non-uniform. This results in the compounds contained in the cartridge being also heated non-uniformly. The nicotine delivery is consequently also non-uniform over consecutive puffs, with a relatively big difference between the first and the last puff; for example, the last puff may contain more than five times the amount of the amount of nicotine contained in the first puff. This in turn leads to unsatisfactory user experience, especially over the first few puffs.

It is desirable to provide a cartridge which would allow a more uniform heating of the compounds contained therein, and therefore also more uniform nicotine delivery in the sense of consistency of nicotine yield per puff.

According to a first aspect of the invention, a cartridge for an aerosol generating device is provided. The cartridge comprises a first cavity containing a nicotine source and a second cavity containing a lactic acid source, the first cavity and the second cavity defining an inner space between the cavities and an outer periphery of the cavities. The cartridge further comprises a susceptor comprising one or more susceptor elements, wherein the susceptor is arranged such that the susceptor is partly positioned in the inner space between the cavities, and partly positioned in the outer periphery of the cavities, the outer periphery of the cavities being a space between the cavity walls and the cartridge walls.

With a cartridge according to the first aspect of the invention, the heating of the cartridge, the cavities or the nicotine source and the lactic acid source is more uniform, leading to improvements in the uniform delivery of nicotine in the sense of consistency of nicotine yield per puff. Embodiments of the invention are described below; various features, or indeed all the features may be combined as appropriate.

As used herein, the 'inner space between the cavities' is a space which is defined between the adjacent walls of the cavities when the cavities are provided adjacent to each other.

The inner space may be defined as a space within the cartridge and between the cavities into which a susceptor element may be positioned such that the distance between the susceptor element and the wall of the first cartridge delimiting the inner space is equal to the distance between the susceptor element and the wall of the second cartridge delimiting the inner space. The cavities themselves are not considered inner space. The susceptor element may be flat or curved.

If the adjacent walls of the cavity are flat and the cavities are of rectangular shape, the inner space between the cavities may be the space defined between the adjacent walls. The inner space between the cavities may be the space delimited by the adjacent walls of the cavities.

If at least one of the adjacent walls is of a shape which is curved or otherwise bent and the wall adjacent the inner space is convex, the inner space between the cavities may be defined by a rectangle or rectangles circumscribed around the curved or bent wall or walls.

In case the cavities are offset, the inner space between the cavities may be defined between the overlapping portions of the cavities, or between adjacent walls of the two cavities.

In case of cavities with substantially circular, oval or elliptic cross section, positioned next to each other so that their longitudinal axes are parallel, the inner space may be defined as follows. The middle point between the cavities lies in the middle of the shortest line connecting the walls of the first cavity and the second cavity, respectively. The inner space may be defined as the space which is less than or equal to a radius distance from the middle point along the parallel axes, and which does not lie within one of the cavities.

In general, the inner space may be defined as follows. The cartridge and the cavities define a longitudinal axis along the length of the cartridge or the cavities, a first transverse axis defining a width of the cartridge or the cavities, and a second transverse axis defining a depth of the cartridge or the cavities. The cavities may be positioned next to each other so that their longitudinal axes are parallel and their first transverse axes are parallel or substantially parallel. The middle point between the cavities lies in the middle of the shortest line connecting the walls of the first cavity and the second cavity, respectively. There is at least one middle point, but there may be more than one middle point. For example, where the cavities have parallel longitudinal axes, the middle point between the two cavities may be a line running parallel to the longitudinal axes of both cavities. The inner space may be defined as the space which is less than or equal to a width distance from the middle point along the first transverse axes, and which does not lie within one of the cavities.

The length of the inner space between the cavities may be at least 50%, at least 80%, or 100% of the length of the cartridge. The width of the inner space, in the first transverse direction, between the cavities may be at least 50%, at least 80%, or 100% of the width of the cartridge, in the first transverse direction.

As used herein, the 'outer periphery of the cavities' is the space around the cavities which is not the inner space. The outer periphery is defined as a space between the cavity walls and the cartridge walls. The susceptor partially positioned in the outer periphery of the cavities does not extend to either the cavity walls or the cartridge walls. The 'outer periphery of the cavities' does not refer to the outer periphery of the cartridge or the outermost portion of the cartridge.

The susceptor may comprise a single piece of material. The susceptor may comprise multiple elements. The susceptor elements may be separate. The susceptor elements may be connected together. The susceptor elements may together form a single piece of material. The susceptor may comprise multiple elements, with some of the susceptor elements being connected together, while other susceptor elements being provided separate from the elements connected together.

The material of the susceptor may be curved or folded such that the susceptor is positioned in the inner space between the cavities as well as at the outer periphery of the cavities. The susceptor may be S-shaped or W-shaped to surround at least a portion of the first cavity and the second cavity, respectively. The susceptor may be provided in the form of two loops surrounding at least a portion of the first cavity and the second cavity, respectively. The susceptor may be provided in the form of three flat elements, with one of the flat elements positioned in the inner space between the cavities, and the other two flat elements positioned in the outer periphery of the cavities such that the cavities are arranged between the susceptor elements. The susceptor may be provided in the form of a three curved elements positioned in the inner space between the cavities, and the other two flat elements positioned in the outer periphery of the cavities such that the cavities are arranged between the susceptor elements. The susceptor may be provided in the form of any number of flat and curved elements, with for example one flat element arranged in the inner space between the cavities and the curved elements positioned in the outer periphery of the cavities. In case of the susceptor or susceptor elements are curved or arched, the susceptor or susceptor elements may be positioned around the cavities, circumscribing at least a portion of the outer periphery of the cavities.

The susceptor or susceptor elements which are provided in the inner space may be provided in such a shape and size that the susceptor or susceptor elements occupy at least 80% of the inner space. The length of the susceptor or susceptor elements which are provided in the inner space may be at least 50%, at least 70%, at least 80% or at least 90% of the length of the cavities. The width of the susceptor or susceptor elements which are provided in the inner space may be at least 50%, at least 70%, at least 80% or at least 90% of the width of the cavities. Each dimension of the susceptor or susceptor elements provided in the inner space may be at least 90% of the corresponding dimension of the cavities.

The length of the susceptor or susceptor elements which are provided in the inner space may be at least 50%, at least 70%, at least 80% or at least 90% of the length of the cartridge. The width of the susceptor or susceptor elements which are provided in the inner space may be at least 50%, at least 70%, at least 80% or at least 90% of the width of the cartridge. Each dimension of the susceptor or susceptor elements provided in the inner space may be at least 90% of the corresponding dimension of the cartridge.

The susceptor or susceptor elements may have the same area as the area of the walls of the cavities adjacent to the susceptor, and may be positioned so that the susceptor or susceptor elements are aligned with the respective adjacent walls of the cavities.

The susceptor or susceptor elements which are provided in the outer periphery may be provided in such a shape and size that the susceptor or susceptor elements occupy at least 50% of the outer periphery of the cavities. The susceptor or susceptor elements which are provided in the outer periphery may be provided in such a shape and size that the susceptor or susceptor elements occupy at least 70%, at least 80% or at least 90% of the outer periphery of the cavities. The length of the susceptor or susceptor elements which are provided in the outer periphery may be at least 50%, at least 70%, at least 80% or at least 90% of the length of the cavities. The width of the susceptor or susceptor elements which are provided in the inner space may be at least 50%, at least 70%, at least 80%, at least 90%, at least 100%, at least 110%, at least 120% or at least 130% of the width of the cavities. Each dimension of the susceptor or susceptor elements provided in the outer periphery may be at least 90% of the corresponding dimension of the cavities. In case of the susceptor or susceptor elements are curved or arched in cross section, 'width' may be understood as the length of the curve or arch.

The thickness of the susceptor or susceptor elements may be around 1 mm, around 0.5 mm, or around 0.3 mm. The thickness of the susceptor or susceptor elements may be the same as the depth of the susceptor cavity; this leads to better heat transfer between the susceptor and the cartridge. The susceptor thickness may be chosen dependent on the material, the expected maximum temperature, and the required time necessary for heating. In general, the thinner the susceptor is, the faster the susceptor heats the contents of the cavities. However, dependent on material of the susceptor, the susceptor may overheat the contents of the cavities. The thicker the susceptor is, the slower the susceptor heats the contents of the cavities is because of thermal inertia of susceptor material.

The susceptor may comprise a first susceptor element and a second susceptor element, wherein the first susceptor element is positioned in the inner space between the cavities, and the second susceptor element is positioned in the outer periphery of the cavities, adjacent to the first cavity, the second cavity, or both the first cavity and the second cavity.

The susceptor may comprise a third susceptor element. There may be three susceptor elements of the same size, positioned parallel to each other. The susceptor may be arranged such that the first cavity is between the first susceptor element and the third susceptor element, and the second cavity is between the first susceptor element and the third susceptor element.

In use, the cartridge is inserted in an aerosol generating device, which comprises a receiving chamber. The receiving chamber is shaped so that the cartridge fits within the chamber.

The aerosol generating device comprises an inductor. During use, the inductor generates an alternating magnetic field to generate eddy currents and hysteresis losses in the susceptor, causing the susceptor to heat up, thereby heating the aerosol-forming substrate.

The inductor used with the susceptor or susceptor elements described above may be provided in the form of an inductor coil. The inductor coil may be disposed around at least a portion of the receiving chamber. A power supply and a controller are connected to the inductor coil and configured to provide an alternating electric current to the inductor coil such that, in use, the inductor coil generates an alternating magnetic field to heat the susceptor or susceptor elements and thereby heat at least a portion of an aerosol-generating article received in the chamber.

The cartridge contains a nicotine source and a lactic acid source. The nicotine source and the lactic acid source are heated as the cartridge is heated. Nicotine vapour released from the nicotine source and lactic acid vapour released from the lactic acid source are conducted to a mixing chamber where they react with one another in the gas phase to form an aerosol comprising nicotine lactate salt particles. The aerosol is then conducted through a mouthpiece and into the user's mouth.

The cartridge may be of any suitable shape. For example, the cartridge may be cylindrical. As used herein, 'cylindrical' or 'cylinder' means a body defined by two end faces and all the points on all the lines between the caps which are parallel to a given line and which pass through a fixed plane curve in a plane not parallel to the given line. For example, the cartridge or any of its parts may be cylindrical with the caps being circular, elliptical, oval, or polygonal with rounded edges. For example, a body having a height and a base which is a trapezoid or a hexagon with rounded edges (or any similar shape) is also a cylinder. A cylinder may comprise circular or curved walls, flat walls, or any combination thereof.

The cartridge may be of any suitable size. The cartridge may have a length of between about 5 mm and about 30 mm. The cartridge may have a length of between about 10 and about 20 mm. The cartridge may have a length of about 13 mm or about 15.4 mm.

The cartridge may have a diameter of, for example, between about 4 mm and about 10 mm. In certain embodiments the cartridge may have a diameter of about 7 mm. The cartridge may have a diameter of about 6.75 mm. The cartridge may have a diameter of about 6.2 mm, for example 6.16 mm. As used herein, 'diameter' means the least upper bound of the set of all distances between pairs of points in a cross section of the cartridge defined by a plane perpendicular to the longitudinal axis of the cartridge.

The cartridge comprises a first cavity and a second cavity for the nicotine source and lactic acid source, respectively. The cartridge may further comprise at least one susceptor cavity accommodating the susceptor or susceptor elements. The cartridge may comprise a single susceptor cavity accommodating a susceptor formed as a single piece of material. The cartridge may comprise a single susceptor cavity accommodating three susceptor elements. The cartridge may comprise three susceptor cavities for accommodating three susceptor elements. The susceptor elements may occupy at least 80% of each respective susceptor cavity.

The susceptor may be positioned so it is in contact with the susceptor cavity walls. For example, the thickness of the susceptor may be the same as the depth of the susceptor cavity, or the susceptor may be tightly fitted into the susceptor cavity. This may improve the heat transfer between the susceptor and the cavities containing nicotine and lactic acid source, respectively.

With a susceptor or susceptor elements positioned as described above, the heating of the nicotine source and the lactic acid source is more uniform. The difference in temperatures at the portion of the cartridge adjacent to the inner space between the cavities and on the side of the cartridge opposite the portion of the cartridge adjacent to the inner space between the cavities is less than when a single susceptor is provided in the inner space between the cavities only. Consequently, the nicotine yield from each puff is more uniform over the consecutive puffs, reaching the maximum (or close to the maximum) yield after 1-3 puffs, and maintaining a more uniform yield thereafter.

The cartridge may be formed as a single piece. The cartridge may comprise multiple pieces.

The cartridge may comprise two complementary parts. The two complementary parts may have a shape of two parts of a cylinder, for example two semi-cylinders. The parts of a cylinder may be substantially as cut along the longitudinal axis of the cylinder. The two parts of a cylinder (for example the two semi-cylinders) may be positioned so that the curved portions of the cylinder are facing away from each other. Each one of the complementary parts comprises one of the first and the second cavity, respectively.

The two complementary parts may be adapted to interlock with each other and thus form the substantially cylindrical cartridge. The two complementary parts may be surrounded by an outer housing. The outer housing may be also cylindrical. The transverse cross section of the outer housing may be of the same shape as the transverse cross section of the two complementary parts assembled together. The transverse cross section of the outer housing may be of different shape from the transverse cross section of the two complementary parts assembled together. For example, the outer housing may have a circular cross section, while the two complementary parts, when assembled together, may be of substantially polygonal cross section, with at least two flat portions and rounded edges.

The two complementary parts forming the cartridge may define a susceptor cavity between them. This susceptor cavity may be less than 1 mm deep, or less than 0.5 mm deep, for example 0.3 mm deep. The depth of the susceptor cavity may be the same as the thickness of the susceptor or susceptor elements, so that the susceptor or susceptor elements are in contact with the susceptor cavity walls. This ensures that the heat generated by the susceptor is transferred through the walls of the susceptor cavity and into the cartridge.

One or both of the two complementary parts may comprise locking features to allow the complementary parts to be assembled together. Each of the two complementary parts may define one additional susceptor cavity in the space which, upon the two complementary parts being assembled, forms part of the outer periphery of the cavities. These susceptor cavities may be of the same dimension or smaller than the susceptor cavity between the complementary parts. For example, each of these two additional susceptor cavities may be 0.2 mm wide. The two complementary parts, when positioned within an outer body, may define space between each complementary part and the outer body.

The cartridge may comprise at least one cap to cover an opening at the cavity end. There may be two caps to cover the two ends of the cartridge. The single cap or at least one of the caps may comprise openings which allow air to enter the cartridge and the generated aerosol to escape the cartridge and proceed into the mouthpiece. In case two caps are provided, both caps may be provided with openings. The number of openings in each of the two caps may be the same. The number of openings in each cap associated with each cavity may be the same. There may be more openings associated with the second cavity than with the first cavity. There may be five openings associated with the second cavity and three openings associated with the first cavity in each one of the caps. There may be one opening associated with the first cavity and two openings associated with the second cavity in each of the caps. Each opening may be e.g. 0.5 mm in diameter. In general, in determining the diameter of the openings, the overall pressure resistance to draw may be considered. The overall pressure resistance to draw is preferably in the range of 40-80 mmWG. In addition, the ratio of opening areas of the two cavities may be also taken into consideration. In particular, this ration preferably guarantees that molar concentration of both components is the same in a mixing chamber, i.e. the part of the device where the nicotine vapour and the lactic acid vapour mix to produce the aerosol containing nicotine lactate salt particles. In this case increased opening area of acid cavity is needed to equilibrate molar concertation of nicotine which has a higher vapour pressure that lactic acid.

Apart from the openings, the caps close and seal the cavities against leaks of the nicotine source and the lactic acid source, respectively. To this end, the caps are provided with protrusions which tightly fit into the openings of the cavities and thus close the cavities. The openings extend through the thickness of the protrusions to provide fluid communication between the cartridge 1 and the outside of the cartridge 1.

The first and the second cavity for the nicotine source and lactic acid source, respectively, may be positioned next to each other. The cavities may be prism-shaped or trapezoid-shaped. The cavities may be circular, elliptic, oval, half-moon shaped, crescent-shaped, or polygon shaped in cross section. In case the cavities have at least one substantially flat wall, the cavities may be positioned such that the flat walls face each other and define the inner space between the cavities. In one embodiment, the cavities are oval-shaped in cross section, positioned such that the long sides of the ovals face each other and define the inner space between the cavities. The cavities may extend along substantially the whole length of the cartridge. In one embodiment, the cavities are oval-shaped in cross section, positioned such that each of the cavities is placed in one part of a cartridge, and such that the long sides of the ovals and the parts of the cartridge face each other and define the inner space between the parts of the cartridge. In a cartridge which is 15.4 mm long and 6.75 mm in diameter, the dimensions of each of the cavities may be 11.6 mm×5 mm×1 mm. The distance between the axes of the cavities may be 2.21 mm, while the distance between the adjacent walls of the cavities may be 1.21 mm.

The nicotine source may comprise one or more of nicotine, nicotine base, a nicotine salt, such as nicotine-HCl, nicotine-bitartrate, or nicotine-ditartrate, or a nicotine derivative. The nicotine source may comprise natural nicotine or synthetic nicotine. The nicotine source may comprise pure nicotine, a solution of nicotine in an aqueous or non-aqueous solvent or a liquid tobacco extract. The nicotine source may further comprise an electrolyte forming compound. The electrolyte forming compound may be selected from the group consisting of alkali metal hydroxides, alkali metal oxides, alkali metal salts, alkaline earth metal oxides, alkaline earth metal hydroxides and combinations thereof. For example, the nicotine source may comprise an electrolyte forming compound selected from the group consisting of potassium hydroxide, sodium hydroxide, lithium oxide, barium oxide, potassium chloride, sodium chloride, sodium carbonate, sodium citrate, ammonium sulphate and combinations thereof. The nicotine source may comprise an aqueous solution of nicotine, nicotine base, a nicotine salt or a nicotine derivative and an electrolyte forming compound. The nicotine source may further comprise other components including, but not limited to, natural flavours, artificial flavours and antioxidants.

The nicotine source and the lactic acid source may be embedded in a carrier material. The carrier material may be a sorption material. The carrier material may be a polymeric matrix. The carrier material may be a soaking or wicking element. The carrier material may be chosen so as to improve heat dissipation. The carrier material may comprise solid porous matrix such as borosilicate glass or quartz. With such matrix, temperature of the matrix becomes more uniform and therefore the evaporation of the nicotine source and the lactic acid source.

The cartridge may be formed from one or more materials that are nicotine-resistant and lactic acid-resistant.

The cartridge may comprise a thermally conductive material. The cartridge may comprise polymer with carbon additives. The cartridge may comprise liquid-crystal polymers (LCP) filled with graphite powder. The concentration of the filling material may be e.g. 30%. The cartridge may comprise liquid-crystal polymers (LCP) in combination with conductive glass beads. The glass beads may be embedded in the LCP. The glass beads may be positioned within the material of the cartridge, between the outer walls of the cartridge and the outer walls of the cavities containing nicotine and lactic acid source. The above described composition of the cartridge may help to homogenize temperature in the nicotine source and the lactic acid source, respectively, as compared with cartridges made of plastic (LCP, PEEK) without fillers and without the glass beads. This leads to a more even heating of the nicotine and the lactic acid sources.

As used herein with reference to the present invention, the term "aerosol-generating device" refers to a device which is configured to interact with an aerosol-generating article comprising a nicotine source and a lactic acid source to generate an aerosol comprising nicotine lactate salt particles. The aerosol generating device, which comprises a receiving chamber, into which the cartridge is inserted. The aerosol generating device comprises a power source and a source of magnetic field, for example an inductor coil which, upon switching the device on, provides a varying magnetic field to the susceptor. The susceptor is thus heated and heats the cartridge.

In a second aspect of the invention, a cartridge for an aerosol generating device is provided. The cartridge comprises a first cavity containing a nicotine source, a second cavity containing a lactic acid source, the first cavity and the second cavity comprising a thermally conductive material.

The cartridge may comprise polymer containing carbon additives. The cartridge may comprise liquid-crystal polymers (LCP) filled with graphite powder. This may help to homogenize temperature in the nicotine source and the lactic acid source, respectively, as compared with cartridges made of plastic (LCP, PEEK) without fillers.

In a third aspect of the invention, a cartridge for an aerosol generating device is provided. The cartridge comprises a first cavity containing a nicotine source, a second cavity containing a lactic acid source. The nicotine source and the lactic acid source are embedded in a carrier material chosen so as to improve heat dissipation. The carrier material may comprise solid porous matrix such as borosilicate glass or quartz. With such matrix, temperature of the matrix becomes more uniform and therefore the evaporation of the nicotine source and the lactic acid source.

Specific embodiments of the present invention will now be described, by way of example only, with reference to the accompanying drawings in which:

FIG. 1*a* is an overview of a cartridge according to the present invention;

FIG. 1*b* is a front view of the cartridge;

FIG. 2 is a longitudinal cross section along line II-II of the cartridge;

FIG. 3 is a transverse cross section along line III-III of the cartridge;

FIGS. 4*a* to 4*e* show several various arrangements of a susceptor in the cartridge;

FIG. 5 is an overview of one component of the cartridge;

FIG. 9 is a schematic view of an aerosol-generating device which the cartridge may be used with.

An exemplary embodiment of a cartridge 1 according to the present invention is shown in the Figures. The cartridge 1 comprises a body 2, an upper cap 3 and a lower cap 5.

The body 2 accommodates a first piece 11 and a second piece 12. Each of the pieces 11, 12 accommodates a cavity 13, 14. The first piece 11 accommodates a first cavity 13. The first cavity 13 contains a nicotine source. The second piece 12 accommodates a second cavity 14. The second cavity 14 contains a lactic acid source.

Figure 7:
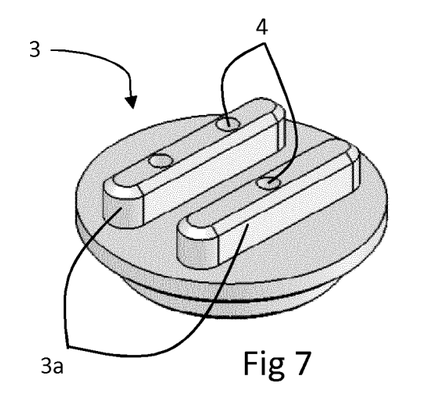
FIG. 7 is an overview of an upper cap of the cartridge.
Figure 8:
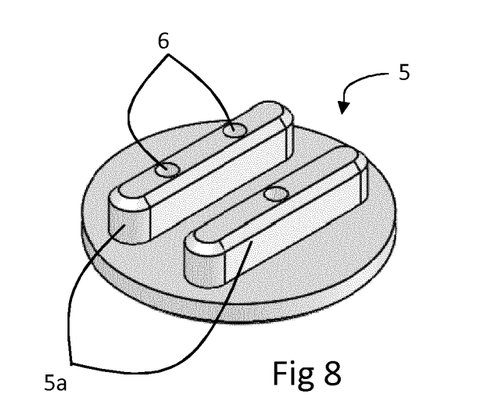
FIG. 8 is an overview of the lower cap of the cartridge.

Each of the upper cap 3 and the lower cap 5 (shown in FIGS. 7 and 8) comprises openings 4, 6. The openings 4, 6 provide a fluid communication channel between the respective cavities 13, 14 and the outside of the cartridge 1. One opening 4 in the upper cap 3 and one opening 6 in the lower cap 5 are associated with the first cavity 13. Two openings 4 in the upper cap 3 and two openings 6 in the lower cap 5 are associated with the second cavity 14. Apart from the openings 4, 6, the caps 3, 5 close and seal the cavities 13, 14 against leaks of the nicotine source and the lactic acid source, respectively. To this end, protrusions 3a, 5a are provided, which are inserted into the openings of the cavities 13, 14. The holes 4, 6 extend through the thickness of the protrusions 3a, 5a to provide fluid communication between the cavities 13, 14 and the outside of the cartridge 1.

Figure 6:
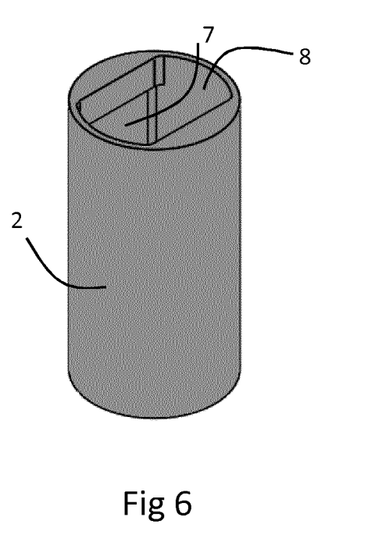
FIG. 6 is an overview of an outer body of the cartridge.

The outer surface of the body 2 is cylindrical, with a circular cross section. The inner surface of the body 2 has two flat portions 7 facing each other and two curved portions 8 facing each other. The curved portions 8 form a section of a circle with a diameter smaller than the circle formed by the outer surface. The curved portions 8 connect the flat portions 7, and the flat portions 7 together with the curved portions 8 form a cylinder with non-circular cross section. The inside space of the body 2, defined by the cylinder with non-circular cross section, is empty before the cartridge 1 is assembled, and is adapted to accommodate the two pieces 11, 12.

Figure 5:
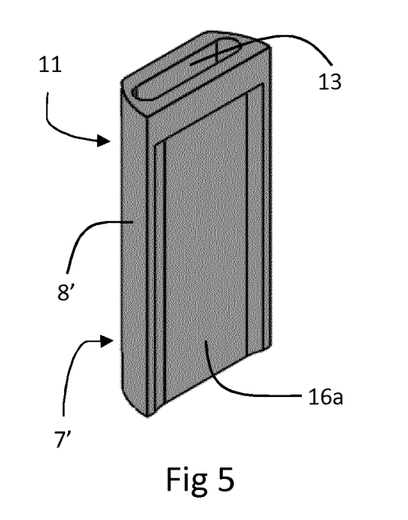

The two pieces 11, 12 are configured to be assembled together and, when assembled, to fit into the inside space of the body 2. Each of the two pieces 11, 12 comprises two curved portions 8', a flat portion 7', and a face 16a, 16b. The flat portion 7' and the face 16a, 16b are positioned opposite each other. When the two pieces 11, 12 are assembled together, faces 16a, 16b face each other and define between themselves a susceptor cavity 16, while the flat portions 7' face away from each other. When the two pieces 11, 12 are assembled together and put into the housing 2, the two pieces 11, 12 are positioned such that the flat portions 7' face the flat portions 7 provided on the inner surface of the body 2, and the curved portions 8' are in contact with the curved portions 8 provided on the inner surface of the body 2. The flat portions 7, 7' face each other, but they are not in full contact, and they define susceptor cavities 15, 17 between themselves.

Each of the two pieces 11, 12 of the cartridge 1 accommodates a cavity 13, 14. The cavities 13, 14 are oval shaped. The two pieces 11, 12 define a longitudinal axis which is parallel to the flat face 7' and the face 16a, 16b. The longitudinal axis of the oval is parallel to the longitudinal axis of the two pieces 11, 12. The cavities are positioned parallel to each other. The susceptor cavities 15, 16 and 17 are parallel to each other and parallel to the susceptor cavities 15, 16, 17.

Figure 1A:
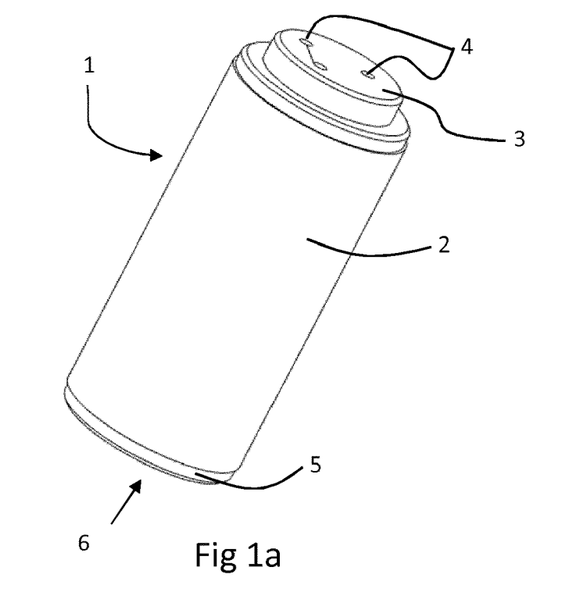
Figure 1B:
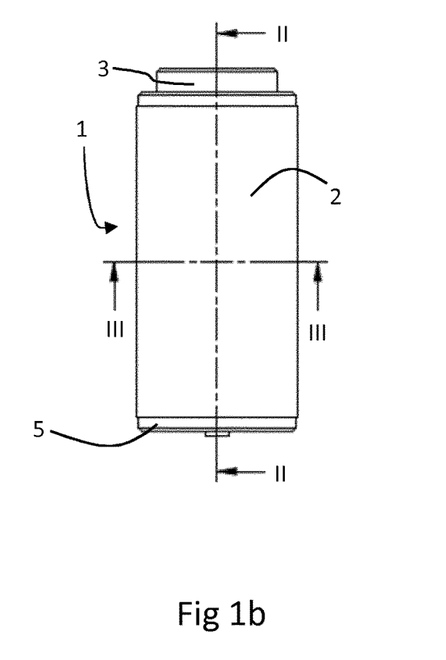
Figure 2:
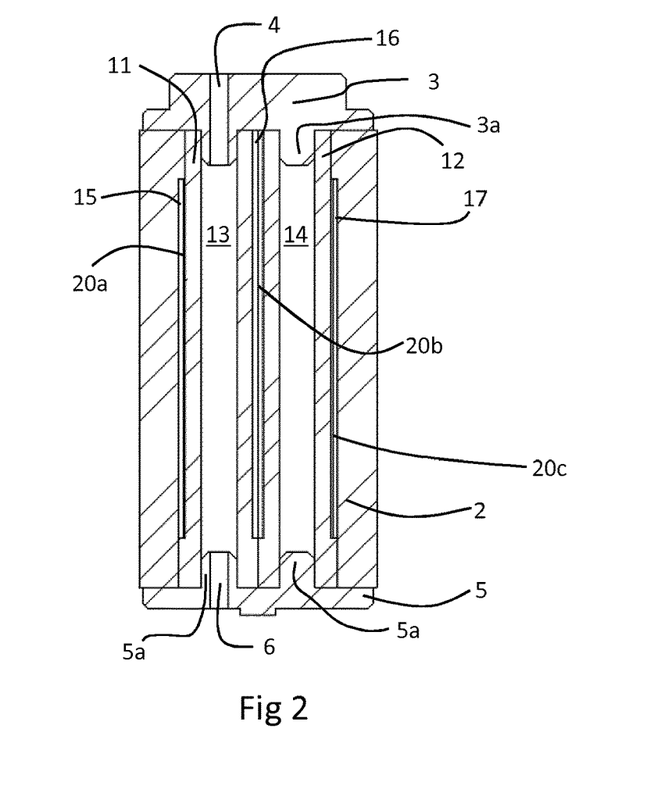
Figure 3:
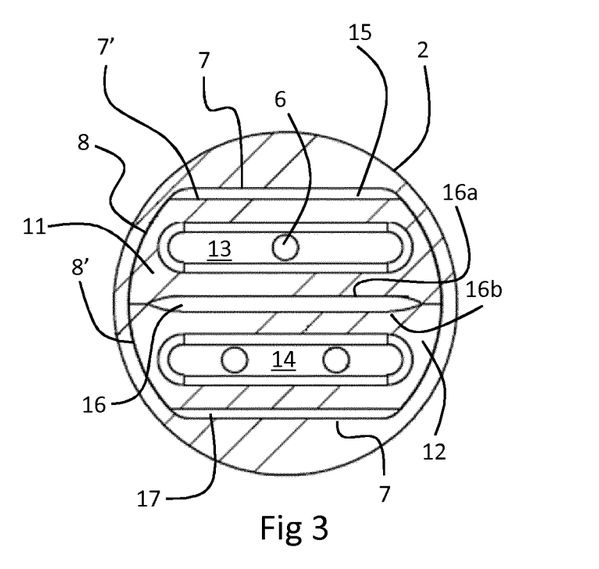
Figure 4A:
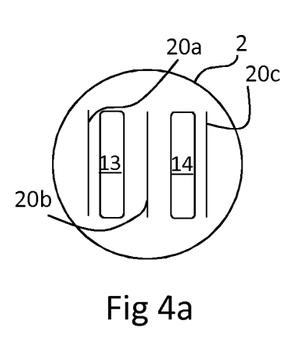

In a first configuration, shown in FIG. 4a, the susceptor 20 has three susceptor elements 20a, 20b, 20c. Each of the susceptor elements 20a, 20b, 20c is positioned within one of the susceptor cavities 15, 16, 17, respectively. The susceptor elements 20a, 20b, 20c are flat rectangular elements. The area of each of the susceptor elements 20a, 20b, 20c is comparable to the area of the respective susceptor cavity 15, 16, 17. For example, each of the susceptor elements 20a, 20b, 20c may cover 90% of the area of the respective susceptor cavity 15, 16, 17. In other words, the oval shaped cavities 13, 14 define a longitudinal cross section with maximum area. The susceptor elements 20a, 20b, 20c are of such size, and are placed in the susceptor cavities 15, 16, 17 such that the area of the susceptor elements covers at least 90% of the longitudinal cross section with maximum area of the cavities 15, 16, 17.

Once the two pieces 11, 12 and the susceptor elements 20a, 20b, 20c are in place inside the body 2, and the cavities 13, 14 are filled with the nicotine source and the lactic acid source, respectively, the cartridge 1 is closed with the upper cap 3 and the lower cap 5. The cartridge 1 may then be used with an aerosol-generating device.

Alternative configurations of the susceptor are shown schematically in FIGS. 4b, 4c, 4d and 4e. The cartridges used with these susceptor configurations are similar to the cartridge 1 described above; appropriate modifications are made to the susceptor cavities to have a shape which can accommodate the susceptor shown in FIGS. 4b-4d. In each of these configurations, the susceptor is positioned such that the long sides of the cavities 13, 14 are overlapped with the susceptor.

Figure 4B:
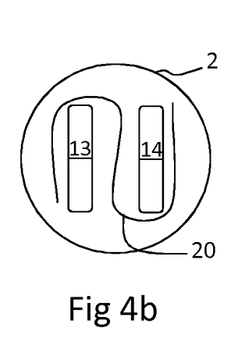

In a second configuration of the susceptor, shown in FIG. 4b, the susceptor is a single S-shaped piece.

Figure 4C:
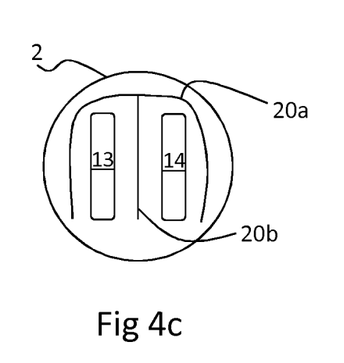

In a third configuration of the susceptor, shown in FIG. 4c, the susceptor comprises three susceptor elements 20a, 20b, 20c, which are connected together to form a W-shape.

Figure 4D:
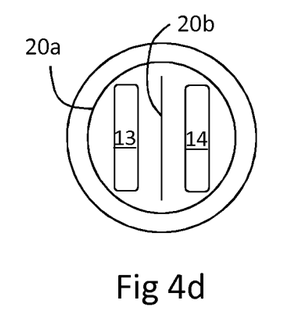

In a fourth configuration of the susceptor, shown in FIG. 4d, the susceptor is provided in the form of a circular susceptor element 20a, which circumscribes the cavities, and an intermediate susceptor element 20b, which is positioned in the space between the cavities 13, 14. The susceptor element 20b is not connected to the susceptor element 20a.

Figure 4E:
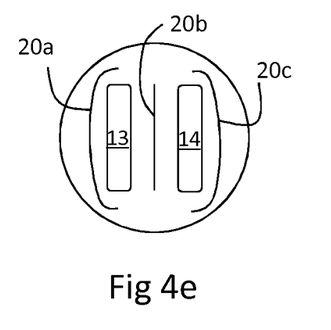

In a fifth configuration, shown in FIG. 4e, the susceptor is provided in the form of three elements 20a, 20b, 20c. The elements 20a, 20c which are positioned in the outer periphery of the cavities are curved. The element 20b is flat.

Embodiment shown in FIG. 4a has good heating efficiency. Embodiments shown in FIGS. 4b and 4c may in some circumstances be easier or cheaper to manufacture.

In use, the cartridge 1 is inserted in an aerosol generating device 100 (FIG. 9), which comprises a receiving chamber 101. The receiving chamber 101 is shaped so that the cartridge 1 fits within the receiving chamber 101. The aerosol generating device 100 comprises an inductor coil 102, which is disposed around the receiving chamber 101. A power supply 103 and a controller 104 provide an alternating electric current to the inductor coil 102. The inductor coil 102 thus generates an alternating magnetic field to heat the susceptor or susceptor elements 20 described above and thereby heat at least a portion of the cartridge 1 received in the chamber 101.

Figure 9:
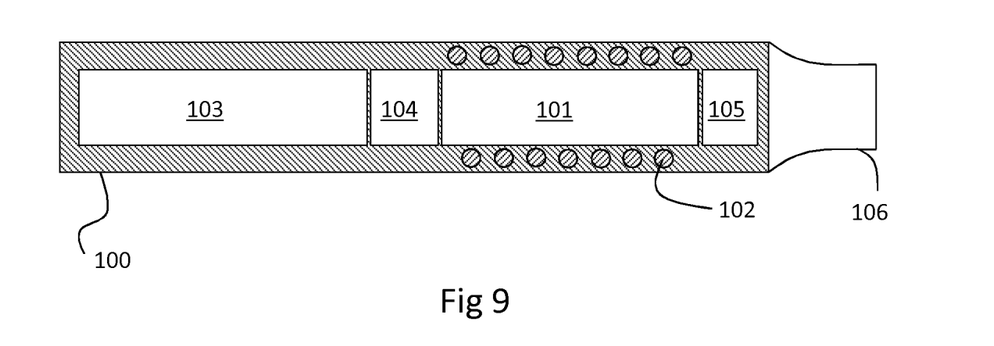

The cavities 13, 14 in the cartridge 1 are contain a nicotine source and a lactic acid source, respectively. The nicotine source and the lactic acid source are heated as the cartridge 1 is heated. Nicotine vapour released from the nicotine source and lactic acid vapour released from the lactic acid source are conducted to a mixing chamber 105 where they react with one another in the gas phase to form an aerosol comprising nicotine lactate salt particles. The aerosol is then conducted through a mouthpiece 106 and into the user's mouth.

The invention claimed is:

1. A cartridge for an aerosol generating device, comprising:
   a first cavity containing a nicotine source and a second cavity containing a lactic acid source, the first cavity and the second cavity defining an inner space between the cavities and an outer periphery of the cavities; and
   a susceptor comprising one or more susceptor elements, wherein the susceptor is arranged such that the susceptor is partly positioned in the inner space between the cavities, and partly positioned in the outer periphery of the cavities, the outer periphery of the cavities being a space between the cavity walls and the cartridge walls.

2. The cartridge of claim 1 wherein the susceptor comprises a first susceptor element and a second susceptor element, and wherein
   the first susceptor element is positioned in the inner space between the cavities, and
   the second susceptor element is positioned in the outer periphery of the cavities, adjacent to the first cavity, the second cavity, or both the first cavity and the second cavity.

3. The cartridge of claim 2 wherein the susceptor comprises a third susceptor element.

4. The cartridge of claim 3 wherein the susceptor is arranged such that
   the first susceptor element is positioned in the inner space between the first cavity and the second cavity,
   the first cavity is between the first susceptor element and the second susceptor element, and
   the second cavity is between the first susceptor element and the third susceptor element.

5. The cartridge of claim 3 wherein the first cavity and the second cavity have an oval-shaped cross section and are positioned such that the elongated axes of the ovals are parallel, wherein the cavities are substantially overlapping, and wherein the first, second and third susceptor element are positioned parallel to the cavities.

6. The cartridge of claim 1 wherein the cartridge is cylindrical and wherein the transverse cross section of the cartridge is circular or hexagonal.

7. The cartridge of claim 1 wherein the cartridge comprises a thermally conductive material.

8. The cartridge of claim 7 wherein the thermally conductive material comprises polymer containing carbon additives.

9. The cartridge of claim 7 wherein the thermally conductive material comprises liquid-crystal polymers (LCP) filled with graphite powder or with conductive glass beads.

10. The cartridge of claim 1 wherein the nicotine source and the lactic acid source are embedded in a carrier material.

11. The cartridge of claim 10 wherein the carrier material may comprise solid porous matrix.

12. The cartridge of claim 11, wherein the solid porous matrix comprises borosilicate glass or quartz or a combination of borosilicate glass and quartz.

13. The cartridge of claim 1, wherein the susceptor is in contact with the susceptor cavity walls.

14. An aerosol generating system comprising an aerosol generating device and the cartridge of claim 1; the aerosol generating device comprising a body, a mouthpiece, a power source and a magnetic field source, wherein the body comprises a receiving chamber configured to receive the cartridge.

15. The aerosol generating system of claim 14, wherein the magnetic field source comprises an inductor coil and the device comprises a controller connected to the inductor coil, wherein the controller is configured to provide an alternating electric current to the inductor coil such that, in use, the inductor coil generates an alternating magnetic field to heat the susceptor element and thereby heat at least a portion of the cartridge.

* * * * *